(12) United States Patent
Takagi et al.

(10) Patent No.: US 8,444,857 B2
(45) Date of Patent: May 21, 2013

(54) METHOD FOR PURIFYING FLUORINATED COMPOUND

(75) Inventors: Hirokazu Takagi, Tokyo (JP); Ryuji Seki, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 160 days.

(21) Appl. No.: 12/963,737

(22) Filed: Dec. 9, 2010

(65) Prior Publication Data

US 2011/0082272 A1    Apr. 7, 2011

Related U.S. Application Data

(63) Continuation of application No. PCT/JP2009/061344, filed on Jun. 22, 2009.

(30) Foreign Application Priority Data

Jun. 24, 2008 (JP) ................................. 2008-164312

(51) Int. Cl.
*C08F 2/16* (2006.01)

(52) U.S. Cl.
USPC ............ 210/643; 526/214; 560/184; 562/580

(58) Field of Classification Search ... 210/643; 526/214; 562/580; 560/184
See application file for complete search history.

(56) References Cited

U.S. PATENT DOCUMENTS

| | | | |
|---|---|---|---|
| 2005/0150833 A1 * | 7/2005 | Funaki et al. ................. | 210/643 |
| 2007/0015864 A1 * | 1/2007 | Hintzer et al. ................ | 524/544 |
| 2007/0015937 A1 | 1/2007 | Hintzer et al. | |
| 2007/0025902 A1 | 2/2007 | Hintzer et al. | |
| 2007/0027251 A1 | 2/2007 | Hintzer et al. | |
| 2010/0113679 A1 | 5/2010 | Hintzer et al. | |

FOREIGN PATENT DOCUMENTS

| | | |
|---|---|---|
| EP | 1 679 298 A1 | 7/2006 |
| EP | 1679298 A1 * | 7/2006 |
| JP | 6-25072 | 2/1994 |
| JP | 7-53465 | 2/1995 |
| JP | 2004-506708 | 3/2004 |
| JP | 2006-321797 | 11/2006 |
| JP | 2007-099624 | 4/2007 |
| JP | 2007-283224 * | 11/2007 |
| WO | 02/26687 | 4/2002 |
| WO | 2007/046345 | 4/2007 |

OTHER PUBLICATIONS

Extended European Search Report issued May 24, 2011, in Application No. / Patent No. 09770126.2-2103 / 2298726 PCT/JP 2009061344.
Neal O. Brace, "Some Approaches to the Synthesis of Fluorinated Alcohols and Esters. I. Completely Fluorinated Esters from the Hunsdiecker Reaction of Silver F-Alkanoates with Iodine", Journal of Fluorine Chemistry, Elsevier, vol. 18, XP007918584, Jan. 1, 1981, pp. 515-524.
International Search Report issued Sep. 15. 2009 in PCT/JP09/061344 filed Jun. 22, 2009.

* cited by examiner

*Primary Examiner* — Peter D. Mulcahy
*Assistant Examiner* — Henry Hu
(74) *Attorney, Agent, or Firm* — Oblon, Spivak, McClelland, Maier & Neustadt, L.L.P.

(57) ABSTRACT

A method for purifying a fluorinated carboxylic acid having an etheric oxygen atom and its derivative, with small decomposition and inclusion of impurities. A liquid containing at least one member selected from the group consisting of a fluorinated compound represented by application formulae (1) and (2) is held at a heating temperature of at most 150° C. and distilled. Further, the liquid is a liquid obtained from any of a waste liquid after an aqueous emulsion of a fluoropolymer is coagulated and the fluoropolymer is separated, an aqueous liquid obtained by cleaning an exhaust gas in a step of drying and/or a step of heat treatment of the separated fluoropolymer, and a liquid obtained by cleaning an anion exchange resin which has been brought into contact with the waste liquid or an aqueous dispersion obtained from the aqueous emulsion of the fluoropolymer, with an alkaline aqueous solution.

10 Claims, No Drawings

METHOD FOR PURIFYING FLUORINATED COMPOUND

This application is a Continuation of PCT/JP09/61344 filed Jun. 22, 2009. Priority to Japan 2008-164312, filed Jun. 24, 2008, is claimed.

TECHNICAL FIELD

The present invention relates to a method for purifying a fluorinated compound selected from a fluorinated carboxylic acid having an etheric oxygen atom and its derivative.

BACKGROUND ART

For production of a fluoropolymer such as polytetrafluoroethylene (hereinafter referred to as PTFE) as a non-melt processable fluororesin, a melt processable fluororesin or a fluorinated elastomer, aqueous emulsion polymerization is applied. In the aqueous emulsion polymerization of a fluoromonomer, in order that the polymerization reaction may not be inhibited by chain transfer, as an emulsifier, ammonium perfluorooctanoate (hereinafter referred to as APFO) which is a fluorinated emulsifier has been commonly used. Further, also in suspension polymerization of PTFE, such a fluorinated emulsifier is added in an extremely small amount at the time of polymerization for the purpose of improving powder properties of a product. However, high bioaccumulation potential of APFO has been pointed out, and disposal of hardly decomposable APFO has been considered to be environmentally problematic, and thus a fluorinated emulsifier which replaces APFO has been required. In recent years, it has been proposed that an ammonium salt of a fluorinated carboxylic acid having an etheric oxygen atom is effective as a fluorinated emulsifier having low bioaccumulation potential as compared with APFO, and its application to aqueous emulsion polymerization and suspension polymerization is in progress (the following Patent Documents 1 and 2). Further, the following Patent Document 3 reports a novel method for producing a fluorinated carboxylate having an etheric oxygen atom.

The ammonium salt of a fluorinated carboxylic acid having an etheric oxygen atom is contained, like APFO, in a waste liquid after an aqueous emulsion of a fluoropolymer is coagulated and the fluoropolymer is separated, after used for the production of the fluoropolymer, and an exhaust gas in a step of drying and/or a step of heat treatment of the separated fluoropolymer, and is preferably recovered and reused.

Further, the ammonium salt of a fluorinated carboxylic acid having an etheric oxygen atom is contained in a liquid obtained by cleaning an anion exchange resin which has been brought into contact with the waste liquid, with an alkaline aqueous solution. Further, the ammonium salt of a fluorinated carboxylic acid having an etheric oxygen atom is contained in a liquid obtained by cleaning an anion exchange resin which has been brought into contact with an aqueous dispersion obtained by adding a nonionic surfactant to the aqueous emulsion of the fluoropolymer, with an alkaline aqueous solution. It is desired to recover and reuse the ammonium salt of a fluorinated carboxylic acid having an etheric oxygen atom also from these liquids.

Heretofore, to recover APFO used for the production of a fluoropolymer, a method of adding an acid to APFO in the aqueous medium to liberate perfluorooctanoic acid (hereinafter referred to as PFOA), and reacting it with an alcohol to form an ester, which is obtained by distillation, a method of acidifying an aqueous solution containing APFO with an acid, followed by heating and separation into two layers, and subjecting the obtained organic liquid to steam distillation to recover PFOA, a method of acidifying a sodium salt of PFOA, decomposing concomitants and impurities with an oxidizing agent, followed by distillation to recover PFOA, etc., have been known (the following Patent Documents 4, 5 and 6).

However, if the conventional method effective for APFO is applied to recovery of a fluorinated carboxylic acid having an etheric oxygen atom as it is, the obtained fluorinated carboxylic acid having an etheric oxygen atom contains a large amount of organic impurities. The organic impurities are difficult to remove after conversion to a fluorinated carboxylate and have influences over the surface tension lowering properties of the fluorinated carboxylate, and if such a fluorinated carboxylate is used as an emulsifier for a fluoromonomer, there are such problems that the polymerization stability is insufficient, an obtainable fluoropolymer will be colored, and the quality will be decreased.

Patent Document 1: WO2007/046345
Patent Document 2: US2007/0015864
Patent Document 3: JP-A-2006-321797
Patent Document 4: JP-A-7-53465
Patent Document 5: JP-A-2004-506708
Patent Document 6: JP-A-6-25072

DISCLOSURE OF THE INVENTION

Object to be Accomplished by the Invention

Under these circumstances, it is an object of the present invention to solve the above problems and to provide an industrially and economically advantageous method for purifying a fluorinated carboxylic acid having an etheric oxygen atom and its derivative.

Means to Accomplish the Object

The present inventors have confirmed that as disclosed in the above Patent Document 3, e.g. by a production method using a fluorinated carboxylate having a relatively high purity as a starting material, a fluorinated carboxylic acid having a relatively high purity is obtained by a distillation/purification step. Whereas, they have found that the fluorinated carboxylic acid once used as e.g. an emulsifier for emulsion polymerization of a fluoropolymer is recovered from the process for producing the fluoropolymer, in a step of distillation/purification of the fluorinated carboxylic acid having an etheric oxygen atom, concomitants and impurities included in the process for producing the fluoropolymer tend to inhibit purification of the fluorinated carboxylic acid or to accelerate its decomposition. The present invention has been accomplished on the basis of these discoveries.

That is, the present invention provides the following method for purifying a fluorinated compound.

[1] A method for purifying a fluorinated compound, which comprises distilling a liquid containing at least one member selected from the group consisting of a fluorinated compound represented by the following formula (1) and a fluorinated compound represented by the following formula (2) by holding it at a heating temperature of at most 150° C.:

wherein $R^F$ is a linear or branched monovalent fluoroorganic group which may have an etheric oxygen atom in its main chain, $R^1$ is a linear or branched bivalent organic group, and $R^2$ is a linear or branched monovalent organic group.

[2] The method for purifying a fluorinated compound according to the above [1], wherein the liquid is a liquid obtained from any of a waste liquid after an aqueous emulsion of a fluoropolymer is coagulated and the fluoropolymer is separated, an aqueous liquid obtained by cleaning an exhaust gas in a step of drying and/or a step of heat treatment of the separated fluoropolymer and a liquid obtained by cleaning an anion exchange resin which has been brought into contact with the waste liquid or an aqueous dispersion obtained from the aqueous emulsion of the fluoropolymer, with an alkaline aqueous solution.

[3] The method for purifying a fluorinated compound according to the above [1] or [2], wherein the fluorinated compound represented by the above formula (1) is a fluorinated compound obtained by adding an acid to a fluorinated compound represented by the following formula (3):

$$[R^F OR^1 COO]_m X^{m+} \tag{3}$$

wherein $R^F$ is a linear or branched monovalent fluoroorganic group which may have an etheric oxygen atom in its main chain, $R^1$ is a linear or branched bivalent organic group, X is a m-valent metal ion, an ammonium ion or an alkyl-substituted ammonium ion, and m is an integer of from 1 to 3.

[4] The method for purifying a fluorinated compound according to any one of the above [1] to [3], wherein the fluorinated compound represented by the above formula (2) is a fluorinated compound obtained by an esterification reaction of the fluorinated compound represented by the above formula (1) with an alcohol represented by $R^2OH$ (wherein $R^2$ is a linear or branched monovalent organic group).

[5] The method for purifying a fluorinated compound according to any one of the above [1] to [4], wherein the fluoropolymer is a homopolymer or copolymer of tetrafluoroethylene.

[6] The method for purifying a fluorinated compound according to any one of the above [1] to [5], wherein the heating temperature is at most 130° C.

[7] The method for purifying a fluorinated compound according to any one of the above [1] to [6], wherein the fluorinated compound represented by the above formula (1) is a fluorinated compound represented by the following formula (4):

$$R^{F2}(O(CF_2)_p)_n OCF_2 COOH \tag{4}$$

wherein $R^{F2}$ is a linear or branched $C_{1-6}$ perfluoroalkyl group, p is an integer of from 1 to 5, and n is an integer of from 0 to 5.

[8] A method for emulsion polymerization of a fluoromonomer, which comprises using, as an emulsifier, a fluorinated compound represented by the following formula (5) obtained by reacting the fluorinated compound represented by the above formula (1) and/or the fluorinated compound represented by the above formula (2) purified by the method for purifying a fluorinated compound as defined in any one of the above [1] to [7], with a compound forming an ion represented by $Y^+$:

$$R^F OR^1 COO^- Y^+ \tag{5}$$

wherein $R^F$ is a linear or branched monovalent fluoroorganic group which may have an etheric oxygen atom in its main chain, $R^1$ is a linear or branched bivalent organic group, and $Y^+$ is $Li^+$, $Na^+$, $K^+$ or $NH_4^+$.

Effects of the Invention

According to the method for purifying a fluorinated compound of the present invention, a fluorinated compound represented by the above formula (1) or (2) can be purified from a liquid obtained from any of a waste liquid after an aqueous emulsion of a fluoropolymer is coagulated and the fluoropolymer is separated, an aqueous liquid obtained by cleaning an exhaust gas in a step of drying and/or a step of heat treatment of the separated fluoropolymer, and a liquid obtained by cleaning an anion exchange resin which has been brought into contact with the waste liquid or an aqueous dispersion obtained from the aqueous emulsion of the fluoropolymer, with an alkaline aqueous solution. Further, by distilling the liquid by holding it to a heating temperature of at most 150° C., the fluorinated compound can efficiently be purified while suppressing decomposition of the fluorinated carboxylic acid by concomitants and impurities included in the process for producing the fluoropolymer. As a result, a high purity fluorinated carboxylic acid having an etheric oxygen atom and its derivative with a low content of organic impurities, can be obtained with a high distillation yield. Further, a high quality fluoropolymer excellent in the polymerization stability can be obtained by emulsion polymerization of a fluoromonomer using as an emulsifier a fluorinated compound obtained by salifying such a fluorinated carboxylic acid having an etheric oxygen atom or its derivative.

BEST MODE FOR CARRYING OUT THE INVENTION

In this description, "a fluorinated compound represented by the formula (n) (n is an optional symbol)" will sometimes be referred to simply as "a fluorinated compound (n)". Further, "an organic group" means a group containing a carbon atom and at least one type of an atom other than the carbon atom. "A fluoroorganic group" is an organic group having a part of or the entire portion capable of being substituted by a fluorine atom, substituted by a fluorine atom(s). "A portion capable of being substituted by a fluorine atom" is a hydrogen atom(s) bonded to a carbon atom.

"Polyfluoro" means that at least two hydrogen atoms bonded to the carbon atom are substituted by fluorine atoms, and "perfluoro" means that all hydrogen atoms bonded to the carbon atom are substituted by fluorine atoms.

"An etheric oxygen atom" means an oxygen atom forming an ether bond (C—O—C), and "an etheric oxygen atom-containing saturated hydrocarbon group" means a saturated hydrocarbon group having at least 2 carbon atoms, having an etheric oxygen atom inserted between the carbon atoms.

"A partially halogenated saturated hydrocarbon group" means a group having a part of hydrogen atoms in a saturated hydrocarbon group substituted by a halogen atom(s) other than a fluorine atom.

"An etheric oxygen atom-containing partially halogenated saturated hydrocarbon group" means a group having a part of hydrogen atoms in an etheric oxygen atom-containing saturated hydrocarbon group substituted by a halogen atom(s) other than a fluorine atom.

In the present invention, the fluorinated compound represented by the formula (1) is a fluorinated carboxylic acid having an etheric oxygen atom. Further, the fluorinated compound represented by the formula (2) is a fluorinated carboxylate having an etheric oxygen atom.

$$R^F OR^1 COOH \tag{1}$$

$$R^F OR^1 COOR^2 \tag{2}$$

In the above formulae, $R^F$ is a linear or branched monovalent fluoroorganic group which may have an etheric oxygen atom in its main chain, $R^1$ is a linear or branched bivalent organic group, and $R^2$ is a linear or branched monovalent organic group.

The monovalent fluoroorganic group is preferably a fluorinated saturated organic group, more preferably a polyfluoro saturated organic group, most preferably a perfluoro saturated organic group.

The monovalent fluorinated saturated organic group may be a fluorinated saturated hydrocarbon group, an etheric oxygen atom-containing fluorinated saturated hydrocarbon group, a partially halogenated fluorinated saturated hydrocarbon group or an etheric oxygen atom-containing partially halogenated fluorinated saturated hydrocarbon group.

The monovalent fluorinated saturated hydrocarbon group may, for example, be a fluorinated alkyl group, a fluorinated cycloalkyl group or a fluorinated saturated hydrocarbon group having a cyclic structure (for example, a cycloalkyl group having an alkyl group as a substituent, an alkyl group having a cycloalkyl group as a substituent, or a group having such a group as a partial structure), and is preferably a fluorinated alkyl group.

The monovalent etheric oxygen atom-containing fluorinated saturated hydrocarbon group may, for example, be a group having an etheric oxygen atom inserted in the carbon-carbon bond of a fluorinated alkyl group having at least 2 carbon atoms or a group having an etheric oxygen atom inserted in the carbon-carbon bond of a cycloalkyl group.

As specific examples of $R^F$, polyfluoroalkyl groups such as $CH_2F-$, $CHF_2-$, $CH_2FCH_2-$, $CH_3CHF-$, $CH_2FCHF-$, $CHF_2CH_2-$, $CH_3CF_2-$, $CF_3CH_2-$, $CHF_2CHF-$, $CH_2FCF_2-$, $CF_3CHF-$ and $CHF_2CF_2-$; perfluoroalkyl groups such as $CF_3-$, $CF_3CF_2-$, $CF_3CF_2CF_2-$, $CF_3CF_2CF_2CF_2-$, $(CF_3)_2CF-$, $(CF_3)_2CFCF_2-$, $CF_3CF_2CF(CF_3)-$ and $(CF_3)_3C-$; and etheric oxygen atom-containing perfluoroalkyl groups such as $CF_3OCF_2-$, $CF_3OCF_2OCF_2-$, $CF_3OCF_2OCF_2OCF_2-$, $CF_3OCF_2OCF_2OCF_2OCF_2-$, $CF_3CF_2OCF_2-$, $CF_3CF_2OCF_2OCF_2-$, $CF_3CF_2OCF_2OCF_2OCF_2-$, $CF_3CF_2OCF_2OCF_2OCF_2OCF_2-$, $CF_3CF_2OCF_2OCF_2OCF_2OCF_2OCF_2-$, $CF_3CF_2CF_2OCF_2-$, $CF_3CF_2CF_2OCF_2OCF_2-$, $CF_3CF_2CF_2OCF_2OCF_2OCF_2-$, $CF_3CF_2CF_2OCF_2OCF_2OCF_2OCF_2-$, $CF_3CF_2CF_2OCF_2OCF_2OCF_2OCF_2OCF_2-$, $CF_3OCF_2CF_2-$, $CF_3OCF_2CF_2OCF_2CF_2-$, $CF_3OCF_2CF_2OCF_2CF_2OCF_2CF_2-$, $CF_3OCF_2CF_2OCF_2CF_2OCF_2CF_2OCF_2CF_2-$, $CF_3OCF_2CF_2OCF_2CF_2OCF_2CF_2OCF_2CF_2OCF_2CF_2-$, $CF_3CF_2OCF_2CF_2-$, $CF_3CF_2OCF_2CF_2OCF_2CF_2-$, $CF_3CF_2OCF_2CF_2OCF_2CF_2OCF_2CF_2-$, $CF_3CF_2OCF_2CF_2OCF_2CF_2OCF_2CF_2OCF_2CF_2-$, $CF_3CF_2OCF_2CF_2OCF_2CF_2OCF_2CF_2OCF_2CF_2OCF_2CF_2-$, $CF_3CF_2CF_2OCF_2CF_2-$, $CF_3CF_2CF_2OCF_2CF_2OCF_2CF_2-$, $CF_3CF_2CF_2OCF_2CF_2OCF_2CF_2OCF_2CF_2-$, $CF_3CF_2CF_2OCF_2CF_2OCF_2CF_2OCF_2CF_2OCF_2CF_2-$, $CF_3CF_2CF_2OCF_2CF_2OCF_2CF_2OCF_2CF_2OCF_2CF_2OCF_2CF_2-$, $CF_3OCF_2CF_2CF_2-$, $CF_3O[CF(CF_3)CF_2O]_bCF(CF_3)CF_2-$ (wherein b is an integer of at least 0, preferably an integer of from 0 to 5), $CF_3CF_2O[CF(CF_3)CF_2O]_bCF(CF_3)CF_2-$ (wherein b is an integer of at least 0, preferably an integer of from 0 to 5), and $CF_3CF_2CF_2O[CF(CF_3)CF_2O]_bCF(CF_3)CF_2-$ (wherein b is an integer of at least 0, preferably an integer of from 0 to 5) may be mentioned.

$R^F$ is preferably a linear perfluoroalkyl group, in view of excellent surface tension lowering properties. $R^F$ is more preferably a monovalent fluoroorganic group represented by $R^{F2}(O(CF_2)_p)_n$, wherein $R^{F2}$ is a linear or branched $C_{1-6}$ perfluoroalkyl group, p is an integer of from 1 to 5, and n is an integer of from 0 to 5.

$R^1$ is a bivalent organic group, preferably a bivalent fluoroorganic group, more preferably a linear perfluoroalkylene group in view of excellent surface tension lowering properties, most preferably $CF_2$. As specific examples of $R^1$, alkylene groups such as $-CH_2-$, $-CH_2CH_2-$ and $-CH_2CH_2CH_2-$; polyfluoroalkylene groups such as $-CHF-$, $-CH_2CHF-$, $-CHFCH_2-$, $-CHFCHF-$, $-CHFCF_2-$ and $-CF_2CHF-$; and perfluoroalkylene groups such as $-CF_2CF_2-$, $-CF(CF_3)-$, $-CF(CF_3)CF_2-$, $-CF_2CF(CF_3)-$, $-CF(CF_3)CF_2CF_2-$, $-CF_2CF(CF_3)CF_2-$, $-CF_2CF_2CF(CF_3)-$ and $-(CF_2)_d-$ (wherein d is an integer of at least 1, preferably an integer of from 1 to 8) may be mentioned.

In the present invention, the fluorinated compound (1) has a total number of carbon atoms of preferably from 5 to 10, more preferably from 5 to 8, most preferably from 5 to 6.

As specific examples of the compound (1), the following fluorinated carboxylic acids are preferred.

$CF_3CF_2CF_2OCHFCF_2COOH$, $CF_3CF_2OCF_2CF_2COOH$, $CF_3CF_2CF_2OCF_2CF_2COOH$, $CF_3CF_2CF_2COCF_2CF_2COOH$, $(CF_3)_2CFOCF_2COOH$, $(CF_3)_2CFCF_2OCF_2COOH$, $CF_3CF_2CF(CF_3)OCF_2COOH$, $(CF_3)_3COCF_2COOH$, $CF_3OCF_2OCF_2COOH$, $CF_3OCF_2OCF_2OCF_2COOH$, $CF_3OCF_2OCF_2OCF_2OCF_2COOH$, $CF_3OCF_2OCF_2OCF_2OCF_2OCF_2COOH$, $CF_3OCF_2OCF_2OCF_2OCF_2OCF_2OCF_2COOH$, $CF_3CF_2OCF_2OCF_2COOH$, $CF_3CF_2OCF_2OCF_2OCF_2COOH$, $CF_3CF_2OCF_2OCF_2OCF_2OCF_2COOH$, $CF_3CF_2OCF_2OCF_2OCF_2OCF_2OCF_2COOH$, $CF_3CF_2CF_2OCF_2OCF_2COOH$, $CF_3CF_2CF_2OCF_2OCF_2OCF_2COOH$, $CF_3CF_2CF_2OCF_2OCF_2OCF_2OCF_2COOH$, $CF_3CF_2CF_2CF_2OCF_2OCF_2COOH$, $CF_3CF_2CF_2OCF_2COOH$, $CF_3CF_2CF_2OCF(CF_3)COOH$, $CF_3CF_2CF_2OCF_2CF_2COOH$, $CF_3CF_2CF_2OCF_2OCF_2COOH$, $CF_3OCF_2CF_2OCF_2CF_2COOH$, $CF_3CF_2OCF_2CF_2OCF_2COOH$, $CF_3CF_2OCF(CF_3)COOH$, $CF_3CF_2OCF_2CF_2OCF_2CF_2OCF_2COOH$, $CF_3CF_2CF_2OCF_2CF_2OCF_2COOH$, $CF_3OCF_2CF_2OCF_2COOH$, $CF_3CF_2CF_2OCF_2CF_2OCF_2COOH$, $CF_3CF_2CIF_2OCF_2CF_2CF_2OCF_2COOH$, $CF_3OCF_2CF_2CF_2OCF(CF_3)COOH$, $CF_3OCF_2CF_2CF_2OCF_2CF_2COOH$, $CF_3OCF_2CF_2CF_2OCF_2COOH$, $CF_3OCF_2CF_2CF_2OCHFCOOH$, $CF_3OCF_2CF_2CF_2OCHFCF_2COOH$, $CF_3OCF(CF_3)CF_2OCF(CF_3)COOH$, $CF_3OCF(CF_3)CF_2OCF_2CF_2COOH$, $CF_3OCF(CF_3)CF_2OCHFCF_2COOH$, $CF_3CF_2OCF(CF_3)CF_2OCF(CF_3)COOH$ and $CF_3CF_2CIF_2OCF(CF_3)CF_2OCF(CF_3)COOH$.

The fluorinated compound (1) is more preferably a fluorinated compound represented by the following formula (4).

$$R^{F2}(O(CF_2)_p)_n OCF_2COOH \qquad (4)$$

wherein $R^{F2}$ is a linear or branched $C_{1-6}$ perfluoroalkyl group, p is an integer of from 1 to 5, and n is an integer of from 0 to 5.

As specific examples of the fluorinated compound (4), $CF_3CF_2OCF_2CF_2OCF_2COOH$, $CF_3CF_2CF_2OCF_2CF_2OCF_2COOH$, $CF_3OCF_2CF_2OCF_2COOH$, $CF_3CF_2CF_2CF_2OCF_2CF_2COOH$, $CF_3CF_2CF_2CF_2OCF(CF_3)COOH$, $CF_3OCF_2CF_2CF_2OCF(CF_3)COOH$, $CF_3OCF_2CF_2CF_2OCF_2COOH$, $CF_3CF_2CF_2CF_2OCF_2COOH$, $CF_3CF_2CF_2OCF_2CF_2COOH$, $CF_3CF_2OCF_2CF_2COOH$, $CF_3OCF_2CF_2COOH$, $CF_3OCF_3OCF_3OCF_2COOH$ and $CF_3OCF_3OCF_3OCF_3OCF_2COOH$ may be mentioned, and $CF_3CF_2OCF_2CF_2OCF_2COOH$ is most preferred.

In the method for purifying a fluorinated compound of the present invention, the fluorinated compound (1) is preferably a fluorinated compound obtained by adding an acid to the following fluorinated compound (3).

$$[R^FOR^1COO^-]_m X^{m+} \quad (3)$$

wherein $R^F$ is a linear or branched monovalent fluoroorganic group which may have an etheric oxygen atom in its main chain, $R^1$ is a linear or branched bivalent organic group, X is a m-valent metal ion, an ammonium ion or an alkyl-substituted ammonium ion, and m is an integer of from 1 to 3.

$R^F$ and $R^1$ are as defined for the fluorinated compound (1). Further, as specific examples of $X^{m+}$, $Li^+$, $Na^+$, $K^+$, $Ca^{2+}$, $Mg^{2+}$, $Al^{3+}$, $NH_4^+$, $NH_3(CH_3)^+$, $NH_2(CH_3)_2^+$, $NH(CH_3)_3^+$ and $N(CH_3)_4^+$ may be mentioned As specific examples of the fluorinated compound (3), a $NH_4$ salt, a Na salt, a K salt, an Al salt, etc. of the fluorinated compound (1) may be preferably mentioned.

In the method for purifying a fluorinated compound of the present invention, the fluorinated compound (2) is preferably a fluorinated compound obtained by an esterification reaction of the fluorinated compound (1) with an alcohol represented by $R^2OH$ (wherein $R^2$ is a linear or branched monovalent organic group).

$R^2$ is preferably an organic group having a short chain length. As specific examples of $R^2$, $C_{1-3}$ alkyl groups such as $-CH_3$, $-CH_2CH_3$ and $-CH(CH_3)_2$ may be mentioned. When $R^2$ is a $C_{1-3}$ alkyl group, the fluorinated compound (2) has a low boiling point, and thus purification by distillation is easily carried out.

The total number of carbon atoms in the fluorinated compound (2) is preferably from 6 to 11, more preferably from 6 to 9, most preferably from 6 to 7. As specific examples of the fluorinated compound (2), a methyl ester, an ethyl ester, etc. of the fluorinated compound (1) may be preferably mentioned.

In the method for purifying a fluorinated compound of the present invention, the liquid containing at least one member selected from the group consisting of the fluorinated compound (1) and the fluorinated compound (2) is a liquid obtained from any of a waste liquid after an aqueous emulsion of a fluoropolymer is coagulated and the fluoropolymer is separated, an aqueous liquid obtained by cleaning an exhaust gas in a step of drying and/or a step of heat treatment of the separated fluoropolymer, and a liquid obtained by cleaning an anion exchange resin which has been brought into contact with the waste liquid or an aqueous dispersion obtained from the aqueous emulsion of the fluoropolymer, with an alkaline aqueous solution.

The alkaline aqueous solution to clean the anion exchange resin may, for example, be preferably sodium hydroxide, potassium hydroxide, rubidium hydroxide, cesium hydroxide or lithium hydroxide, and among them, sodium hydroxide or potassium hydroxide is preferred.

The fluoropolymer may be PTFE which is a homopolymer of tetrafluoroethylene or a copolymer with a monomer (excluding tetrafluoroethylene) copolymerizable with tetrafluoroethylene. Such a copolymerizable monomer may be a fluoromonomer such as vinylidene fluoride, hexafluoropropylene, chlorotrifluoroethylene or a perfluoro (alkyl vinyl ether) represented by $CF_2=CFOR_f$ (wherein $R_f$ is a $C_{1-16}$ perfluoroalkyl group which may have an etheric oxygen atom), a hydrocarbon olefin such as ethylene, propylene or isobutene, or a hydrocarbon monomer which may have an etheric oxygen atom, such as an alkyl vinyl ether. The copolymer with a monomer copolymerizable with tetrafluoroethylene may be a fluororesin such as a tetrafluoroethylene/hexafluoropropylene copolymer (FEP), a tetrafluoroethylene/perfluoro(alkyl vinyl ether) copolymer (PFA) or an ethylene/tetrafluoroethylene copolymer (ETFE). Further, a fluororesin such as polyvinylidene fluoride (PVDF) or polychlorotrifluoroethylene (PCTFE), or a fluororesin such as ethylene/chlorotrifluoroethylene (ECTFE), obtained by polymerizing a fluoromonomer, may be mentioned. Further, a fluororubber such as a vinylidene fluoride/hexafluoropropylene copolymer or a tetrafluoroethylene/propylene copolymer may also be mentioned.

The fluoropolymer is preferably a homopolymer or copolymer of tetrafluoroethylene.

In a conventional method, the aqueous emulsion of a fluoropolymer is produced by polymerizing a fluoromonomer in the presence of an aqueous medium, a polymerization initiator and a fluorinated compound (3) as an emulsifier, in the form of an aqueous emulsion having the fluoropolymer dispersed as fine particles. In a waste liquid obtained after the aqueous emulsion is coagulated and the fluoropolymer is separated, the fluorinated compound (3) remains in a content of usually at a level of from 10 ppm to 10,000 ppm. Further, when the separated fluoropolymer after coagulation is dried and/or subjected to heat treatment by an apparatus such as an oven, an exhaust gas containing a very small amount of droplets of the fluorinated compound (3) is discharged from the heat treatment apparatus. The fluorinated compound (3) is contained also in a cleaning liquid used to clean the exhaust gas. On the other hand, a waste liquid from which the fluoropolymer is separated is obtained also in such a manner that the above-described aqueous emulsion or a waste liquid after the aqueous emulsion is coagulated and the fluoropolymer is separated, is brought into contact with an anion exchange resin e.g. by a method disclosed in JP-A-2007-283224 or WO2007/043278 so that the fluorinated compound (3) is adsorbed in the anion exchange resin, and then the fluorinated compound (3) is desorbed by using an alkaline aqueous solution. In such a waste liquid, the fluorinated compound (3) is contained in an amount of usually from 1 mass ppm to 20 mass %.

Further, in a case where the fluoropolymer is PTFE, a fluoropolymer low concentration dispersion obtained by adding an anionic surfactant to the aqueous emulsion of the fluoropolymer is brought into contact with an anion exchange resin to let the fluorinated compound (3) contained be adsorbed to obtain a fluoropolymer low concentration dispersion having a remarkably low content of the fluorinated compound (3). Then, the fluoropolymer low concentration dispersion is concentrated to industrially produce a fluoropolymer dispersion containing the fluoropolymer in an amount of about 60 mass %. Also from the anion exchange resin in which the fluorinated compound (3) is adsorbed, as described above, the fluorinated compound (3) is desorbed by using an alkaline aqueous solution to obtain a liquid containing the fluorinated compound (3).

The waste liquid or the cleaning liquid containing the fluorinated compound (3) can be concentrated by distilling off water under reduced pressure e.g. by a method disclosed in WO2004/000734 as the case requires. On that occasion, it is preferred to preliminarily coagulate non-coagulated fine particle of the fluoropolymer, whereby coagulation of non-coagulated fine particle of the fluoropolymer while bringing in the fluorinated compound to be purified, along with concentration.

Further, in a case where the fluorinated compound (3) is a $NH_4$ salt or the like which tends to sublimate or is an Al salt or the like which has low solubility, the type of the salt may be converted to e.g. a Na salt, whereby solubility in an aqueous solvent can be increased, and loss by sublimation can be prevented when water is distilled off under reduced pressure. Further, by adding an acid to the waste liquid, the cleaning liquid or the concentrated liquid containing the fluorinated compound (3), the fluorinated compound (3) can be converted to the fluorinated compound (1) to obtain a liquid containing the fluorinated compound (1). The acid is preferably an inorganic acid which itself cannot be an organic impurity, and HCl, $H_2SO_4$, $HNO_3$, etc. are preferably used. HCl having a low boiling point is particularly preferred since it can be easily separated by distillation from the fluorinated compound (1) by distillation of the liquid containing the fluorinated compound (1). Further, the pH of the waste liquid, the cleaning liquid and the concentrated liquid containing the fluorinated compound (3) after addition of the acid is preferably at most 2, more preferably at most 1, most preferably at most 0, whereby the conversion ratio of the fluorinated compound (3) to the fluorinated compound (1) can be made high. When the pH is at most 0, the conversion ratio of the fluorinated compound (3) to the fluorinated compound (1) is usually at least 90 mol %.

The fluorinate compound (1) is also preferably extracted from the liquid containing the fluorinated compound (1) with an organic solvent as the case requires. The organic solvent is preferably a nonaqueous organic solvent, and chloroform, dichloroethylene, methylene chloride, hexane, benzene, toluene, CFC-113, HCFC-225ca, HCFC-225cb, HCFC-123, HCFC-141b, $C_6F_{13}H$, $C_8F_{18}$, $CF_3(CF_2)_4CH_3$, $CF_3(CF_2)_4CH_2CH_3$, $CF_3(CF_2)_5CH_2CH_3$, $CF_3CF_2CH_2CF_2H$, $CF_3(CF_2)_3OCH_3$, $CF_3(CF_2)_3OCH_2CH_3$, $CF_3CH_2OCF_2CF_2H$, perfluoro(2-butyl tetrahydrofuran), perfluoro(2-propyl tetrahydrofuran), etc. are preferably used.

The organic solvent is preferably a fluorinated hydrocarbon in view of excellent solubility of the fluorinated compound (1), more preferably a fluorinated hydrocarbon having an etheric oxygen atom. As specific examples, $CF_3(CF_2)_3OCH_3$, $CF_3(CF_2)_3OCH_2CH_3$ and $CF_3CH_2OCF_2CF_2H$ may be mentioned. In the method for purifying a fluorinated compound of the present invention, the liquid containing the fluorinated compound (2) is preferably obtained by an esterification reaction of the liquid containing the fluorinated compound (1) with $R^2OH$. The fluorinated compound (2), which is an esterified product of the fluorinated compound (1), has low corrosion properties and a low viscosity, and accordingly distillation operation is easily carried out. As the liquid containing the fluorinated compound (1), the above-described liquid obtained by adding an acid to the liquid containing the fluorinated compound (3), which is converted to the fluorinated compound (1), may be used. The temperature at the esterification reaction is preferably at least 0° C., more preferably at least 30° C., most preferably at least 50° C., and further, preferably at most 100° C., in view of excellent reactivity.

The fluorinated compound (2) is also preferably extracted from the liquid to containing the fluorinated compound (2) with an organic solvent as the case requires.

The organic solvent is preferably a nonaqueous organic solvent, and as specific examples, the same organic solvent as the above organic solvent used for extraction of the fluorinated compound (1) from the liquid containing the fluorinated compound (1) may be used. Particularly, a fluorinated hydrocarbon is preferred in view of excellent solubility of the fluorinated compound (2), and a fluorinated hydrocarbon having an etheric oxygen atom is more preferred. As specific examples, $CF_3(CF_2)_3OCH_3$, $CF_3(CF_2)_3OCH_2CH_3$ and $CF_3CH_2OCF_2CF_2H$ may be mentioned.

In the method for purifying a fluorinated compound of the present invention, a liquid containing at least one member selected from the group consisting of the fluorinated compound (1) and the fluorinated compound (2) is distilled by holding it at a heating temperature of at most 150° C. The heating temperature is preferably at most 130° C., more preferably at most 100° C. The heating temperature is properly determined considering the efficiency of the distillation and is not particularly limited, but is preferably at least 10° C., more preferably at least 20° C., most preferably at least 30° C.

The distillation pressure is any of reduced pressure, atmospheric pressure and elevated pressure. Further, since the fluorinated compound (1) is acidic and has corrosion properties, the material of a distillation column is preferably glass, stainless steel, haslelloy, fluororesin lining, or the like. Here, the heating temperature means the internal temperature of a kettle of the distillation column. If the heating temperature of the distillation column is higher than 150° C., the fluorinated compound (1) and/or the fluorinated compound (2) is decomposed during the distillation, thus leading to formation of a short chain compound by breakage of the ether bond or formation of impurities having no carbonyl group by decarboxylation, whereby it will be difficult to purify the fluorinated compound (1) and/or the fluorinated compound (2) with high purity. Further, the distillation yield will also be decreased. In a case where a relatively pure fluorinated compound (1) or fluorinated compound (2) is purified by distillation, such problems will not develop (the above Patent Document 3). Accordingly, the above decomposition and inclusion of impurities are considered to be due to action of concomitants and impurities such as metal ions and organic acids included by means of a step of emulsion polymerization of the fluoropolymer.

The above liquid is, as mentioned above, preferably a liquid obtained from any of a waste liquid after an aqueous emulsion of a fluoropolymer is coagulated and the fluoropolymer is separated, an aqueous liquid obtained by cleaning an exhaust gas in a step of drying and/or a step of heat treatment of the separated fluoropolymer, and a liquid obtained by cleaning an anion exchange resin which has been brought into contact with the waste liquid or an aqueous dispersion obtained from the aqueous emulsion of the fluoropolymer, with an alkaline aqueous solution.

In the method for emulsion polymerization of a fluoromonomer of the present invention, the following fluorinated compound (5) obtained by reacting the fluorinated compound (1) and/or the fluorinated compound (2) purified by the above method for purifying a fluorinated compound with a compound forming an ion represented by $Y^+$, is used as an emulsifier.

$$R^F OR^1 COO^- Y^+ \quad (5)$$

wherein $R^F$ is a linear or branched monovalent fluoroorganic group which may have an etheric oxygen atom in its main chain, $R^1$ is a linear or branched bivalent organic group, and $Y^+$ is $Li^+$, $Na^+$, $K^+$ or $NH_4^+$.

The compound forming an ion represented by $Y^+$ may, for example, be LiOH, KOH, NaOH or $NH_4OH$, and is preferably KOH, NaOH, $NH_4OH$, etc. Among them, $NH_4OH$ forming a $NH_4^+$ ion is preferred.

The fluorinated compound (5) has a total number of carbon atoms of preferably from 5 to 10, more preferably from 5 to 8, most preferably from 5 to 6. As specific examples of the compound (5), fluorinated compounds wherein $Y^+$ is $NH_4^+$ are preferred. More preferred are the following fluorinated compounds.

$CF_3CF_2OCF_2CF_2COO^-NH_4^+$
$CF_3CF_2CF_2CF_2OCF_2CF_2COO^-NH_4^+$
$CF_3CF_2CF(CF_3)OCF_2COO^-NH_4^+$
$CF_3OCF_2OCF_2COO^-NH_4^+$
$CF_3OCF_2OCF_2OCF_2COO^-NH_4^+$
$CF_3OCF_2OCF_2OCF_2OCF_2COO^-NH_4^+$
$CF_3OCF_2OCF_2OCF_2OCF_2OCF_2COO^-NH_4^+$
$CF_3OCF_2OCF_2OCF_2OCF_2OCF_2OCF_2COO^-NH_4^+$
$CF_3CF_2OCF_2OCF_2COO^-NH_4^+$
$CF_3CF_2OCF_2OCF_2OCF_2COO^-NH_4^+$
$CF_3CF_2OCF_2OCF_2OCF_2OCF_2COO^-NH_4^+$
$CF_3CF_2OCF_2OCF_2OCF_2OCF_2OCF_2COO^-NH_4^+$
$CF_3CF_2CF_2OCF_2OCF_2COO^-NH_4^+$
$CF_3CF_2CF_2OCF_2OCF_2OCF_2COO^-NH_4^+$
$CF_3CF_2CF_2OCF_2OCF_2OCF_2OCF_2COO^-NH_4^+$
$CF_3CF_2CF_2CF_2OCF_2OCF_2COO^-NH_4^+$
$CF_3CF_2CF_2CF_2OCF_2COO^-NH_4^+$
$CF_3CF_2CF_2CF_2OCF(CF_3)COO^-NH_4^+$
$CF_3CF_2CF_2CF_2OCF_2CF_2COO^-NH_4^+$
$CF_3CF_2CF_2CF_2OCF_2OCF_2OCF_2COO^-NH_4^+$
$CF_3OCF_2CF_2OCF_2CF_2OCF_2COO^-NH_4^+$
$CF_3CF_2OCF_2CF_2OCF_2COO^-NH_4^+$
$CF_3CF_2OCF(CF_3)COO^-NH_4^+$
$CF_3OCF_2CF_2OCF_2CF_2OCF_2COO^-NH_4^+$
$CF_3CF_2CF_2OCF_2CF_2OCF_2COO^-NH_4^+$
$CF_3OCF_2CF_2OCF_2COO^-NH_4^+$
$CF_3CF_2OCF_2CF_2OCF_2COO^-NH_4^+$
$CF_3CF_2CF_2OCF_2CF_2OCF_2COO^-NH_4^+$
$CF_3OCF_2CF_2CF_2OCF(CF_3)COO^-NH_4^+$
$CF_3OCF_2CF_2CF_2OCF_2CF_2COO^-NH_4^+$
$CF_3OCF_2CF_2CF_2OCF_2COO^-NH_4^+$
$CF_3OCF(CF_3)CF_2OCF(CF_3)COO^-NH_4^+$
$CF_3OCF(CF_3)CF_2OCF_2CF_2COO^-NH_4^+$
$CF_3OCF(CF_3)CF_2OCHFCF_2COO^-NH_4^+$
$CF_3CF_2OCF(CF_3)CF_2OCF(CF_3)COO^-NH_4^+$
$CF_3CF_2CF_2OCF(CF_3)CF_2OCF(CF_3)COO^-NH_4^+$

In a case where the purified fluorinated compound (1) and/or fluorinated compound (2) contains organic impurities and has low purity, the purity of the fluorinated compound (5) obtained by reacting the purified fluorinated compound (1) and/or fluorinated compound (2) with the compound forming an ion represented by $Y^+$ (wherein r is $Li^+$, $Na^+$, $K^+$ or $NH_4^+$) is also low.

If the low purity fluorinated compound (5) is used as an emulsifier, the surface tension lowering properties are not sufficient, and the surface tension lowering properties vary according to the lot. Further, if such a fluorinated compound (5) is used for the aqueous emulsion polymerization of a fluoromonomer, the polymerization stability tends to be decreased, or problems will arise such as coloring or a decrease in quality of an obtainable fluoropolymer. Accordingly, in the method of emulsion polymerization of a fluoromonomer of the present invention, the purity of the fluorinated compound (5) is preferably at least 97%, more preferably at least 98%, most preferably at least 99%. Accordingly, the purity of the fluorinated compound (1) and/or the fluorinated compound (2) is preferably at least 97%, more preferably at least 98%, most preferably at least 99%.

According to the method for purifying a fluorinated compound of the present invention, a high purity fluorinated compound (1) and fluorinated compound (2) can be obtained. Further, according to the method for emulsion polymerization of a fluoromonomer of the present invention, which is a method of using, as a polymerization emulsifier for a fluoromonomer, a high purity compound (5) obtained by using the fluorinated compound (1) and/or the fluorinated compound (2) obtained by the method for purifying a fluorinated compound, the polymerization stability will be improved, and a high quality fluoropolymer can be obtained. Such a high quality fluoropolymer is suitable, for example, as a member for a process for producing a semiconductor for which very high cleanness is required.

EXAMPLES

Now the present invention will be described in further detail with reference to Examples. However, it should be understood that the present invention is by no means restricted to such specific Examples.

Example 1

Example for Purification of
$CF_3CF_2OCF_2CF_2OCF_2COOH$ (Step 1-1): Step of removal of non-coagulated PTFE particles from $CF_3CF_2OCF_2CF_2OCF_2COO^-(NH_4)^+$ In accordance with a method disclosed in JP-A-2006-321797, emulsion polymerization of tetrafluoroethylene was carried out using $CF_3CF_2OCF_2CF_2OCF_2COO^-(NH_4)^+$ as an emulsifier. PTFE was coagulated and separated from the obtained aqueous emulsion of PTFE, and then the waste liquid was analyzed. The waste liquid contained 2,100 ppm of non-coagulated PTFE particles (hereinafter referred to as SS) and 1,055 ppm of $CF_3CF_2OCF_2CF_2OCF_2COO^-(NH_4)^+$. To the waste liquid (1,776 kg), a 8 mass % aqueous solution having 204 g of aluminum chloride hexahydrate dissolved in water was added, followed by stirring for 10 minutes to coagulate SS. Then, a 30 mass % sodium hydroxide aqueous solution was added to the waste liquid to adjust the pH of the waste liquid to 8.55, followed by stirring for 30 minutes, whereby the contained $CF_3CF_2OCF_2CF_2OCF_2COO^-(NH_4)^+$ was converted to $CF_3CF_2OCF_2CF_2OCF_2COO^-Na^+$. Further, the waste liquid was subjected to filtration through a 420 mesh filter to remove the coagulated SS. The obtained waste liquid was a colorless and transparent liquid (1,792 kg) containing 10 ppm of SS.

(Step 1-2): Step of concentration of $CF_3CF_2OCF_2CF_2OCF_2COO^-Na^+$ 1,792 kg of the waste liquid obtained in (Step 1-1) was concentrated under reduced pressure by using a heating tube surface evaporating concentrator (manufactured by Sasakura Engineering Co. Ltd., tradename: E:VCC concentrator) equipped with a heat pump while the pressure in the interior of the EVCC concentrator was kept under 20 kPa (gauge pressure, the same applies hereinafter) and the temperature of a circulating liquid in the interior of the EVCC concentrator at 55±2° C. to obtain 37.3 kg of a concentrated liquid (concentration of $CF_3CF_2OCF_2CF_2OCF_2COO^-Na^+$: 5.03 mass %).

(Step 1-3): Step of conversion to $CF_3CF_2OCF_2CF_2OCF_2COOH$ 20.2 kg of the concentrated liquid obtained in (Step 1-2) was charged in a glass reactor equipped with a stirrer and a reflux condenser and stirred, and concentrated hydrochloric acid was dropwise added under normal pressure at 25° C. to adjust the pH to 0, thereby to convert $CF_3CF_2OCF_2CF_2OCF_2COO^-Na^+$ to $CF_3CF_2OCF_2CF_2OCF_2COOH$. Then, 21.1 kg of $CF_3CH_2OCF_2CF_2H$ as an extraction solvent was added under normal pressure at 25° C., followed by stirring for 30 minutes, and further, the liquid was left at rest for 30 minutes, and then separation into two layers was carried out. A $CF_3CH_2OCF_2CF_2H$ layer (22.1 kg) as the lower layer was analyzed by GC (gas chromatography) analysis and as a result, the content of $CF_3CF_2OCF_2CF_2OCF_2COOH$ was 956 g. Further, the extraction ratio from the concentrated liquid obtained in (Step 1-2) was 94.1%.

(Step 1-4): Step of purification by distillation of $CF_3CF_2OCF_2CF_2OCF_2COOH$ 20.0 kg (content of $CF_3CF_2OCF_2CF_2OCF_2COOH$: 865 g) of the lower layer obtained in (Step 1-3) was continuously supplied to a kettle (2 L) of a glass distillation column equipped with a reflux condenser at 10° C. under normal pressure while keeping the internal temperature of the kettle at 70° C. or below, to distill off $CF_3CH_2OCF_2CF_2H$ thereby to concentrate $CF_3CF_2OCF_2CF_2OCF_2COOH$. At a point where $CF_3CH_2OCF_2CF_2H$ did not distill anymore, the pressure of the kettle was gradually decreased from normal pressure to 5 Torr (1 Torr is about 133.322 Pa, the same applies hereinafter), and $CF_3CF_2OCF_2CF_2OCF_2COOH$ was distilled while internal temperature of the kettle was kept at 92° C. or below. The boiling point was 74° C. (30 Torr). The obtained $CF_3CF_2OCF_2CF_2OCF_2COOH$ purified product was a colorless and transparent liquid having a purify of 99.7%, and the yield was 786 g.

Further, the distillation yield was 91%.

Comparative Example 1

Example for Purification of $CF_3CF_2OCF_2CF_2OCF_2COOH$ 2.0 kg (content of $CF_3CF_2OCF_2CF_2OCF_2COOH$: 87 g) of the lower layer obtained in (Step 1-3) in Example 1 was charged in a kettle (2 L) of a glass distillation column equipped with a reflux condenser at 10° C., and purification by distillation was carried out under normal pressure, whereupon the internal temperature of the kettle increased along with the progress of the distillation of $CF_3CH_2OCF_2CF_2H$ and reached 155° C. Then, the pressure of the kettle was gradually decreased from normal pressure to 50 Torr, and $CF_3CF_2OCF_2CF_2OCF_2COOH$ was distilled so that the internal temperature of the kettle was maintained at 155° C., and distillation was continued. As a result, $CF_3CF_2OCF_2CF_2OCF_2COOH$ was decomposed, and formation of $CO_2$ by decarboxylation and formation of $CF_3CF_2OCF_2COOH$ and $CF_3CF_2H$ by breakage of the ether bond were observed. The obtained $CF_3CF_2OCF_2CF_2OCF_2COOH$ fraction had a purity of 90.9%, and the yield was 66 g. Further, the distillation yield was 76%.

Example 2

Example for Purification of $CF_3CF_2OCF_2CF_2OCF_2COOCH_3$ (Step 2-1): Esterification step In (Step 1-4) in Example 1, $CF_3CF_2OCF_2CF_2OCF_2COOH$ (purity: 95.0%, 500 g) obtained by distilling off $CF_3CH_2OCF_2CF_2H$ in the lower layer obtained in (Step 1-3) as the previous step was charged in a glass reactor (2 L) equipped with a stirrer and a reflux condenser, and 140 g of $CH_3OH$ was slowly introduced with stirring so that the internal temperature was kept at 30° C. or below. After the entire amount was introduced, stirring was carried out at 70° C. further for 8 hours to obtain a product. The product was analyzed by gas chromatography and as a result, the content of $CF_3CF_2OCF_2CF_2OCF_2COOCH_3$ was 432 g, and excess $CH_3OH$ and unreacted $CF_3CF_2OCF_2CF_2OCF_2COOH$ were also detected.

(Step 2-2): Step of purification by distillation of $CF_3CF_2OCF_2CF_2OCF_2COOCH_3$ The product obtained in (Step 2-1) was charged in a kettle (1 L) of a glass distillation column equipped with a reflux condenser at 10° C., the pressure of the kettle was gradually decreased from normal pressure to 5 Torr, and purification by distillation was carried out while the internal temperature of the kettle was kept at 120° C. or below. The obtained $CF_3CF_2OCF_2CF_2OCF_2COOCH_3$ purified product was a colorless and transparent liquid having a purity of 99.5%, and the yield was 400 g. Further, the distillation yield was 92%.

Example 3

Emulsion Polymerization of Tetrafluoroethylene

Emulsion polymerization of tetrafluoroethylene was carried out as follows by using the purified $CF_3CF_2OCF_2CF_2OCF_2COOH$ obtained in Example 1.

(Step 3-1): Preparation of $CF_3CF_2OCF_2CF_2OCF_2COO^-(NH_4)^+$

In a glass reactor (2 L) equipped with a stirrer and a reflux condenser, 1,180 g of a 2.5 mass % ammonia water prepared by diluting commercially available ammonia water (28 mass %) was charged. Then, with stirring, 601 g of the purified $CF_3CF_2OCF_2CF_2OCF_2COOH$ obtained in Example 1 was dropwise added under cooling with ice over a period of 2 hours. After completion of the dropwise addition, the temperature was gradually increased and kept at 40° C. for 5 hours. Then, while the concentration (measured by evaporation to dryness) of $CF_3CF_2OCF_2CF_2OCF_2COO^-(NH_4)^+$ and the pH (measured by a pH meter) were measured, the 2.5 mass % ammonia water and water were added little by little and stirred to obtain 2,100 g of an aqueous solution of $CF_3CF_2OCF_2CF_2OCF_2COO^-(NH_4)^+$ having a concentration of 30.0 mass % and a pH of 5.7.

(Step 3-2): Polymerization of tetrafluoroethylene

In a 100 L stainless steel autoclave equipped with a baffle plate and a stirrer, 234 g of the aqueous solution (solid content concentration: 30.0 mass %, pH: 5.7) of $CF_3CF_2OCF_2CF_2OCF_2COO^-(NH_4)^+$ obtained in (Step 3-1), 862 g of paraffin wax (melting point: 52° C.) and 59 L of deionized water were charged. The air in the autoclave was replaced with nitrogen, and then the pressure was reduced, and pressure was increased by adding tetrafluoroethylene (TFE) and the temperature was raised to 70° C. with stirring. Then, the pressure was raised to 1.70 MPa by TFE, and 5.0 g of dissuccinic acid peroxide (concentration: 80 mass%, the rest being water) was dissolved in 1 L of warm water at about 70° C. arid injected into the autoclave. Polymerization was proceeded by adding TFE to keep the inner pressure of the autoclave at 1.70 MPa. In the middle of the polymerization, the above-described $CF_3CF_2OCF_2CF_2OCF_2COO^-(NH_4)^+$ aqueous solution was added in a total amount of 415 g. Further, ammonium sulfite was dissolved in water and added in the middle of the polymerization in a total amount of 3.85 g as ammonium sulfite. The temperature was decreased to 65° C. in the middle of the polymerization and increased to 90° C. at the latter stage of the polymerization. The reaction was terminated at a point where the amount of TFE added reached 22.9 kg, and TFE in the autoclave was released into the atmosphere. The polymerization time was 196 minutes. The obtained PTFE aqueous emulsion was cooled, and the supernatant paraffin wax was removed. The aqueous emulsion had a solid content concentration of 26.2 mass %. Further, the average primary particle size of PTFE fine particles was 0.280 μm. Aggregates in the reactor were just about a trace.

This aqueous emulsion was diluted with pure water to a solid content concentration of 10 mass % and adjusted to 20° C., followed by stirring to coagulate the PTFE fine particles. The obtained PTFE fine powder was dried in an oven at 180° C. for 6 hours. The Yellow Index of the obtained powder was measured by using a color difference meter, whereupon the YI value=−6, and the obtained powder was confirmed to be white without coloring. Further, the standard specific gravity (SSG) was 2.150, and the average particle size was 550 μm.

The number average molecular weight of the PTFE powder as calculated from the heat of the crystallization by the method of Suwa et. al. disclosed in Journal of Applied Polymer Science, 17, 3253 (1973), was about 20,000,000. The obtained PTFE powder can be used for production of a PTFE processed product as it is like conventional PTFE. Further, 1 kg of the obtained PTFE powder was irradiated with 50 kGy of γ rays to obtain a low molecular weight PTFE powder having a number average molecular weight of 25,000. The obtained low molecular weight PTFE powder is suitable as an additive for a plastic, an oil and a coating material.

Example 4

Example for Preparation of $CF_3CF_2OCF_2CF_2OCF_2COOH$ (Step 4-1): Step of removal of non-coagulated tetrafluoroethylene/propylene copolymer particles contained in $CF_3CF_2OCF_2CF_2OCF_2COO^-(NH_4)^+$ aqueous solution In a waste liquid after an aqueous emulsion of a tetrafluoroethylene/propylene copolymer obtained by producing the tetrafluoroethylene/propylene copolymer using $CF_3CF_2OCF_2CF_2OCF_2COO^-(NH_4)^+$ as an emulsifier was coagulated and the tetrafluoroethylene/propylene copolymer was separated, 60 ppm of non-coagulated tetrafluoroethylene/propylene copolymer particles (hereinafter referred to as copolymer SS) were contained. Further, in the waste liquid, the $CF_3CF_2OCF_2CF_2OCF_2COO^-(NH_4)^+$ concentration was 868 ppm, and the pH was 8.6. 1 L of the waste liquid was put in a 2 L glass beaker equipped with a FULLZONE blade, and a 10 mass % hydrochloric acid aqueous solution was added with stirring to adjust the pH to 2. After the pH adjustment, 0.1 g of aluminum chloride hexahydrate was added with stirring by the FULLZONE blade. The amount of added aluminum chloride hexahydrate corresponded to 100 ppm to the total amount of the waste liquid. Immediately after addition of aluminum chloride hexahydrate, coagulation of the copolymer SS started to form a white gelatinous precipitate. Stirring was continued as it was for 10 minutes, and then a 0.1 N sodium hydroxide aqueous solution was added to adjust the pH of the aqueous solution to 10.0, to convert the contained $CF_3CF_2OCF_2CF_2OCF_2COO^-(NH_4)^+$ to $CF_3CF_2OCF_2CF_2OCF_2COO^-Na^+$. Aggregates settled at the bottom of the beaker, arid the supernatant liquid was colorless and transparent.

The supernatant liquid was filtrated through a filter paper with an average aperture of 10 μm and the copolymer SS in the filtrate was measured, whereupon it was 5 ppm. Further, the $CF_3CF_2OCF_2CF_2OCF_2COO^-Na^+$ concentration in the filtrate was 850 ppm.

(Step 4-2): Step of adsorption/desorption of emulsifier $CF_3CF_2OCF_2CF_2OCF_2COO^-Na^+$ in ion exchange resin 1 L of the filtrate obtained in (Step 4-1) was made to pass through a packed column having a capacity of 100 mL filled with 10 mL of a weakly basic ion exchange resin (WA30 manufactured by Mitsubishi Chemical Corporation, hereinafter referred to as IERWA30) at a space velocity SV=5/hr to conduct adsorption operation. The temperature of the filtrate was 25° C. 20 hours was required to make 1 L of the filtrate pass, during which the packed column was not clogged. The aqueous solution after it passed through the packed column, had a $CF_3CF_2OCF_2CF_2OCF_2COO^-Na^+$ concentration of 5 ppm. Then, a 0.1 M sodium hydroxide aqueous solution was made to pass through the packed column at 23° C. at a flow rate of 20 mL/hr to conduct desorption operation of the adsorbed emulsifier The emulsifier is estimated to be bonded to the base in the ion exchange resin as an ion of $CF_3CF_2OCF_2CF_2OCF_2COO^-$ when it is adsorbed. The obtained liquid after desorption had a pH of 10 and had a concentration of $CF_3CF_2OCF_2CF_2OCF_2COO^-Na^+$ of 4.1 mass % in 20 mL. The recovery rate of $CF_3CF_2OCF_2CF_2OCF_2COO^-Na^+$ was 94.5%.

(Step 4-3): Step of conversion to $CF_3CF_2OCF_2CF_2OCF_2COOH$

In accordance with the method disclosed in (Step 1-3), from the liquid obtained after desorption obtained in (Step 4-2), the $CF_3CF_2OCF_2CF_2OCF_2COOH$ concentrated liquid was obtained with a yield of 99%.

(Step 4-4): Step of purification by distillation of $CF_3CF_2OCF_2CF_2OCF_2COOH$ In accordance with the method disclosed in (Step 1-4), from the concentrated liquid obtained in (Step 4-3), a colorless and transparent $CF_3CF_2OCF_2CF_2OCF_2COOH$ purified product (purity: 99.7%) was obtained with a yield of 95%.

Example 5

Example for Purification of $CF_3CF_2OCF_2CF_2OCF_2COOH$ (Step 5-1): Preparation of PTFE aqueous dispersion Into a 100 L stainless steel autoclave equipped with a baffle plate and a stirrer, 36 g of $CF_3CF_2OCF_2CF_2OCF_2COO^-(NH_4)^+$, 555 g of paraffin wax (melting point: 55° C.) and 61.3 litter of deionized water were charged. The air in the autoclave was replaced with nitrogen, and then the pressure was reduced, then a TFE monomer was introduced, and the temperature was raised to 62° C. with stirring. Further, the TFE monomer was injected until the inner pressure became 1.765 MPa, and 26.3 g of dissuccinic acid peroxide (concentration: 80 mass %, the rest being water) was dissolved in 1 liter of warm water at about 70° C. and injected into the autoclave. As the autoclave inner pressure dropped to 1.716 MPa about 3 minutes later, the TFE monomer was injected to keep the inner pressure to 1.765 MPa to proceed the polymerization. In the middle of the polymerization, $CF_3CF_2OCF_2CF_2OCF_2COO^-(NH_4)^+$ was dissolved in warm water and injected in a total amount of 53 g as $CF_3CF_2OCF_2CF_2OCF_2COO^-(NH_4)^+$ dividedly in twice. The autoclave temperature was gradually raised to 72° C., and the reaction was terminated at a point where the amount of the TFE monomer injected reached 22 kg, and TFE in the autoclave was released into the atmosphere. The polymerization time was 105 minutes. After cooling, the paraffin wax solidified at the upper portion was removed to obtain a PTFE aqueous emulsion. The PTFE aqueous emulsion had a PTFE concentration of about 25.0 mass %, a $CF_3CF_2OCF_2CF_2OCF_2COO^-(NH_4)^+$ concentration of 0.40 mass % to the PTFE mass, and the average particle size of the PTFE fine particles was 0.26 μm, the average molecular weight of PTFE was 760,000, and the standard specific gravity of PTFE was 2.21.

Using 10 kg of the PTFE aqueous emulsion, a nonionic surfactant (manufactured by NIPPON NYUKAZAI CO., LTD., tradename "Newcol (trademark) 1308FA", molecular formula: $C_{13}H_{27}-(OC_2H_4)_8-OCH(CH_3)CH_2-OH$, molecular weight: 610) in an amount of 3.0 mass % to the PTFE mass and deionized water (255 g) were added to prepare a PTFE low concentration aqueous dispersion having a PTFE concentration of 24.2 mass %.

(Step 5-2): Step of adsorption/desorption of emulsifier $CF_3CF_2OCF_2CF_2OCF_2COO^-NH_4^+$ in ion exchange resin A connected column comprising two columns (internal capacity: 51 cc) connected in series, each column having a length of 80 cm and an inner diameter of 0.9 cm and filled with a weakly basic anion exchange resin (Lewatit (trademark) manufactured by LANXESS, tradename: MP62WS) was prepared, and 100 ml of a 1.5 mass % aqueous solution of an anionic surfactant (Newcol (trademark), 1308FA) was made to pass at a rate of 50 cc per hour by a tubular pump, and then the PTFE low concentration aqueous dispersion obtained in (Step 5-1) was made to pass at a rate of 120 cc per hour over a period of about 85 hours. In the PTFE low concentration aqueous dispersion, the $CF_3CF_2OCF_2CF_2OCF_2COO^-(NH_4)^+$ concentration was reduced to 0.004 mass % to the PTFE mass.

The PTFE low concentration aqueous dispersion before it passed through the column contained 10 g of $CF_3CF_2OCF_2CF_2OCF_2COO^-(NH_4)^+$ by calculation, and the PTFE low concentration aqueous dispersion after it passed through the column contained about 0.1 g of $CF_3CF_2OCF_2CF_2OCF_2COO^-(NH_4)^+$ by calculation, and accordingly it is considered that 9.9 g of the emulsifier was adsorbed in the anion exchange resin. The emulsifier is estimated to be bonded to the base in the ion exchange resin as an ion of $CF_3CF_2OCF_2CF_2OCF_2COO^-$ when it is adsorbed.

To the obtained PTFE low concentration aqueous dispersion, a non-fluorinated anionic surfactant (sodium lauryl sulfate, tradename "Kao EMAL AD25R", active ingredient: 25 mass %) was added in an amount of 0.2 mass % to the PTFE mass, and by electrophoresis, a voltage of 200 V/m was applied to carry out concentration thereby to obtain a PTFE high concentration aqueous dispersion having a PTFE concentration of about 66.2 mass % and having a surfactant concentration of 2.3 mass % to the PTFE mass.

To this PTFE high concentration aqueous dispersion, Newcol (trademark) 1308FA in an amount of 2.5 mass % to the PTFE mass, a polyethylene oxide (f) (molecular weight: 500,000, manufactured by Wako Pure Chemical Industries, Ltd.) in an amount of 0.1 mass % to the PTFE mass, a 28 mass % ammonia water (2.5 g) in a ratio of 0.05 mass % to the PTFE mass, and deionized water (272 g) were added to obtain a PTFE aqueous dispersion having a PTFE concentration of about 60.8 mass %, a surfactant concentration of 4.9 mass % to the PTFE mass, a $CF_3CF_2OCF_2CF_2OCF_2COO^-(NH_4)^+$ concentration of 0.004 mass % to the PTFE mass, a pH of 9.7 and a viscosity of 22 mPa·s. The emulsifier is estimated to be bonded to the base in the ion exchange resin as an ion of $CF_3CF_2OCF_2CF_2OCF_2COO^-$ when it is adsorbed.

Then, the anion exchange resin was taken out from the column, and the desorption operation of the emulsifier was conducted.

To the anion exchange resin, 100 g of a sodium hydroxide aqueous solution having a concentration of 2.0 mass % was added, followed by heating to a temperature of 60° C. and gentle stirring for 4 hours, and then the anion exchange resin was removed by filtration to obtain 108 g of a sodium hydroxide aqueous solution containing $CF_3CF_2OCF_2CF_2OCF_2COO^-Na^+$. In this aqueous solution, the $CF_3CF_2OCF_2CF_2OCF_2COO^-Na^+$ concentration was 7.8 mass %, which indicates that 85% of the emulsifier was desorbed.

(Step 5-3): Step of conversion to $CF_3CF_2OCF_2CF_2OCF_2COOH$

In accordance with the method disclosed in (Step 1-3), from the liquid obtained after desorption in (Step 5-2), a $CF_3CF_2OCF_2CF_2OCF_2COOH$ concentrated liquid was obtained with a yield of 99%.

(Step 5-4): Step of purification by distillation of $CF_3CF_2OCF_2CF_2OCF_2COOH$ In accordance with the method disclosed in (Step 1-4), from the concentrated liquid obtained in (Step 5-3), a colorless and transparent $CF_3CF_2OCF_2CF_2OCF_2COOH$ purified product (purity: 99.9%) was obtained with a yield of 98%.

Methods for measuring the respective evaluation items are shown below.

(A) Average particle size of PTFE: measured by using a laser scattering particle size partition analyzer (manufactured by HORIBA Ltd., tradename "LA-920").

(B) Standard specific gravity (SSG) of PTFE: measured in accordance with ASTM D1457-91a and ASTM D4895-91a.

(C) Average molecular weight of PTFE: obtained from the amount of latent heat determined by differential thermal analysis of dried PTFE in accordance with the method of Suwa (J. Appl. Polym. Sci, 17, 3253 (1973)).

(D) PTFE concentration and surfactant concentration: about 10 g of each dispersion sample was put in an aluminum dish the mass of which was known, and the mass after drying at 120° C. for one hour and the mass after decomposition of the surfactant after heating at 380° C. for 35 minutes, were obtained, to calculate the PTFE concentration and the surfactant concentration to the PTFE mass. The surfactant concentration in the present invention means a value including the nonionic surfactant, the fluorinated emulsifier and other thermally decomposed components.

(E) pH: measured by the glass electrode method.

(F) Viscosity: measured by using a Brookfield viscometer equipped with a spindle No. 1 at 60 rpm.

Industrial Applicability

According to the present invention, a fluorinated carboxylic acid having an etheric oxygen atom added as an emulsifier for emulsion polymerization of a fluoromonomer, can be recovered with a low content of organic impurities from an aqueous emulsion containing a fluoropolymer, and can be reused as an emulsifier excellent in the polymerization stability.

The entire disclosure of Japanese Patent Application No. 2008-164312 filed on Jun. 24, 2008 including specification, claims and summary is incorporated herein by reference in its entirety.

What is claimed is:

1. A method for recovering a fluorinated compound, which compound is at least one selected from the group consisting of a fluorinated compound represented by formula (1) and a fluorinated compound represented by formula (2):

$$R^F OR^1 COOH \quad (1)$$

$$R^F OR^1 COOR^2 \quad (2)$$

wherein $R^F$ is a linear or branched monovalent fluoroorganic group which may have an etheric oxygen atom in its main chain, $R^1$ is a linear or branched bivalent organic group, and $R^2$ is a linear or branched monovalent organic group, wherein said method comprises distilling:

a waste liquid remaining after an aqueous emulsion of a fluoropolymer is coagulated and the fluoropolymer is separated, or an aqueous liquid obtained by cleaning an exhaust gas originating from drying and/or heat treating a fluoropolymer, or a liquid obtained by cleaning an anion exchange resin with an alkaline aqueous solution, at a heating temperature of at most 150° C., wherein said waste liquid, said aqueous liquid and said liquid obtained by cleaning an anion exchange resin comprise at least one fluorinated compound represented by formula (1) or formula (2).

2. The method for recovering a fluorinated compound according to claim 1, wherein said waste liquid, said aqueous liquid and said liquid obtained by cleaning an anion exchange resin comprise at least one compound of formula (1), and wherein the fluorinated compound represented by formula (1) was produced in said waste liquid, said aqueous liquid and said liquid by adding an acid to a fluorinated compound represented by the following formula (3):

$$[R^F OR^1 COO^-]_m X^{m+} \quad (3)$$

wherein $R^F$ is a linear or branched monovalent fluoroorganic group which may have an etheric oxygen atom in its main chain, R' is a linear or branched bivalent organic group, X is a m-valent metal ion, an ammonium ion or an alkyl-substituted ammonium ion, and m is an integer of from 1 to 3.

3. The method for recovering a fluorinated compound according to claim 1, wherein said waste liquid, said aqueous liquid and said liquid obtained by cleaning an anion exchange resin comprise at least one compound of formula (2), and wherein the fluorinated compound represented by formula (2) was produced in said waste liquid, said aqueous liquid and said liquid obtained by cleaning an anion exchange resin by an esterification reaction of the fluorinated compound represented by formula (1) with an alcohol represented by $R^2 OH$ wherein $R^2$ is a linear or branched monovalent organic group.

4. The method for recovering a fluorinated compound according to claim 1, wherein said method comprises distilling:

a waste liquid remaining after an aqueous emulsion of a fluoropolymer is coagulated and the fluoropolymer is separated, or an aqueous liquid obtained by cleaning an exhaust gas originating from drying and/or heat treating a fluoropolymer, and wherein the fluoropolymer is a homopolymer or copolymer of tetrafluoroethylene.

5. The method for recovering a fluorinated compound according to claim 1, wherein the heating temperature is at most 130° C.

6. The method for recovering a fluorinated compound according to claim 1, wherein the fluorinated compound is a fluorinated compound represented by the following formula (4):

$$R^{F2}(O(CF_2)_p)_n OCF_2 COOH \quad (4)$$

wherein $R^{F2}$ is a linear or branched $C_{1-6}$ perfluoroalkyl group, p is an integer of from 1 to 5, and n is an integer of from 0 to 5, and wherein said waste liquid, said aqueous liquid and said liquid obtained by cleaning an anion exchange resin comprise a fluorinated compound represented by formula (4).

7. The method for recovering a fluorinated compound according to claim 1, wherein the heating temperature is at most 100° C.

8. The method for recovering a fluorinated compound according to claim 1, wherein the heating temperature is at least 30° C.

9. The method for recovering a fluorinated compound according to claim 1, wherein the fluorinated compound is a fluorinated compound represented by the following formula:

$$CF_3 CF_2 OCF_2 CF_2 OCF_2 COOH$$

and wherein said waste liquid, said aqueous liquid and said liquid obtained by cleaning an anion exchange resin comprise a fluorinated compound represented by said formula.

10. The method for recovering a fluorinated compound according to claim 9, wherein the fluorinated compound represented by the formula

CF3CF2OCF2CF2OCF2COOH was produced in said waste liquid, said aqueous liquid and said liquid obtained by cleaning an anion exchange resin by adding an acid to a fluorinated compound represented by the following formula

CF3CF2OCF2CF2OCF2COO—NH4+.

* * * * *